United States Patent
Song

(10) Patent No.: US 8,642,300 B2
(45) Date of Patent: Feb. 4, 2014

(54) METHOD FOR PRODUCTION OF BIO-ETHANOL USING WATERMELON SEEDS

(76) Inventor: Baek Young Song, Daejeon (KR)

( * ) Notice: Subject to any disclaimer, the term of this patent is extended or adjusted under 35 U.S.C. 154(b) by 266 days.

(21) Appl. No.: 13/176,117

(22) Filed: Jul. 5, 2011

(65) Prior Publication Data

US 2012/0045810 A1    Feb. 23, 2012

(30) Foreign Application Priority Data

Aug. 23, 2010 (KR) ........................ 10-2010-0081535

(51) Int. Cl.
*C12P 7/06* (2006.01)
(52) U.S. Cl.
USPC ....................................................... 435/161
(58) Field of Classification Search
USPC ....................................................... 435/161
See application file for complete search history.

(56) References Cited

U.S. PATENT DOCUMENTS 8,183,022 B2 * 5/2012 Steiner ........................ 435/161

\* cited by examiner

*Primary Examiner* — Tekchand Saidha
(74) *Attorney, Agent, or Firm* — The PL Law Group, PLLC

(57) ABSTRACT

Provided is a method for production of bioethanol using watermelon seeds and, more particularly, a method for producing bioethanol with high production yield using watermelon seeds, including: sterilizing watermelon seeds, which are usually discarded as food waste from domestic houses, supermarkets, farm houses, etc., at 121° C. for 10 to 20 minutes under anaerobic conditions; finely grinding the sterilized watermelon seeds; adding glacial acetic acid to the ground seeds to remove linoleic acid therefrom; and inoculating the treated seeds free from linoleic acid with a strain for ethanol fermentation such as *Saccharomyces cerevisiae*, followed by agitating at 25 to 35° C. and 100 to 300 rpm for 5 to 15 days, to conduct fermentation.

8 Claims, No Drawings

METHOD FOR PRODUCTION OF BIO-ETHANOL USING WATERMELON SEEDS

CROSS-REFERENCE TO RELATED APPLICATION

This application claims the benefit of Korean Patent Application No. 10-2010-0081535 filed on Aug. 23, 2010, in the Korean Patent and Trademark Office, the disclosures of which are incorporated herein in their entirety by reference.

BACKGROUND OF THE INVENTION

1. Field of the Invention

The present invention relates to a method of obtaining biofuels from watermelon seeds.

2. Description of the Related Art

Bioethanol is an eco-friendly alternative fuel extracted through fermentation of saccharide or cellulose fractions in plants. As such, bioethanol increasingly draws more attention for its usefulness as an additive in gasoline products, compared to existing biomethanol used as an additive in diesel products.

Since the 1970s, most studies in the development of bioethanol have been implemented in the United States and Brazil, as the main producers. In Brazil, production of bioethanol using sugar cane has been promoted as one of the national policy projects, and about 30% of overall fuel consumption for vehicles has been successfully replaced with bioethanol in 2004. In the United States, it was announced in the President's Annual State of the Union address to Congress in 2008, that oil consumption would be reduced by 20%, replacing oil consumption with the increasing use of alternative energy, such as bioethanol In addition, other countries including, for example, Japan, China, and other Asian nations, are also moving ahead with policies to expand bioethanol production. As such, with increased demand and interest in bioethanol throughout the world, bioethanol production output is gradually increasing.

After the oil crisis in the 1970s, research and development into bioethanol began as a part of an alternative energy development initiative and has mostly been executed with crop biomass obtained from corn, sugar cane, and/or wood-based biomass. Wood-based biomass as raw materials can be obtained from wood resources. In fact, Brazil has succeeded in the commercialization of bioethanol fuel based on the abundant cultivation and supply of sugar cane. Meanwhile, in the United States, plenty of commercial technologies to produce bioethanol utilizing abundant corn and/or wood resources have been accumulated.

However, with regard to crop biomass, ethical problems associated with utilizing invaluable food resources as fuel raw materials has recently been publicized and, in addition, disadvantages related to the production of bioethanol, using such crop biomass, has similarly been encountered with regards to the supply and demand of raw materials, and/or price competitiveness resulting from international grain prices rapidly increasing in early 2008.

Although resources for wood-based biomass have merit in increasing ethanol production yield, in that they are plentiful in nature, cellulose content, and hemi-cellulose content (i.e., the obtained biomass is at least 75%), the wood-based biomass has a physically and chemically rigid structure, compared to crop biomass, thus causing difficulties in chemical and/or enzymatic treatment approaches for the saccharification of cellulose and/or hemi-cellulose. Moreover, since wood-based biomass contains about 15 to 25% lignin, consisting of numerous hydrophobic aromatic compounds, high costs and complicated pre-treatments to remove the said lignin fraction may be required. Furthermore, forest degradation encountered in biomass production also accelerates global warming and causes environmental damage, in turn manifesting in problems with environmental ethics, such as violation of responsibilities related to eco-friendly fuel production.

Accordingly, in order to solve these ethical problems, while overcoming the energy (fuel) crises or exhaustion that mankind is facing, there is a strong need to ensure novel and highly efficient biomass resources capable of replacing existing crop biomass or wood-based biomass resources.

SUMMARY

Accordingly, an aspect of the present invention is to provide an eco-friendly method for production of bioethanol using watermelon seeds that are generally discarded as food waste.

Another aspect of the present invention is to provide a method for the highly efficient production of bioethanol, by removing linoleic acid from watermelon seeds before the ethanol fermentation thereof.

In yet another aspect of the present invention, a method for producing bioethanol is provided without the associated ethical problems such as waste of food resources, compared to the utilization of existing crop biomass or wood-based biomass.

In still yet another aspect of the present invention, yeast strains most effective for the production of bioethanol using watermelon seeds are provided, and a method of maximally producing bioethanol by fermenting the aforementioned yeast strains is also provided.

Another embodiment of the present invention provides a method for the production of bioethanol, including the steps of: sterilizing the watermelon seeds at 121° C. for 10 to 20 minutes under anaerobic conditions; finely grinding the sterilized watermelon seeds; adding glacial acetic acid to the ground watermelon seeds to remove linoleic acid therefrom; and inoculating the linoleic acid-free watermelon seeds with a yeast strain for ethanol fermentation.

According to the foregoing production method, after inoculating the linoleic acid-free seeds with the yeast strain for ethanol fermentation, the inoculated linoleic acid-free seeds may be subjected to fermentation with agitation at 100 to 300 rpm at 25 to 35° C. for 5 to 15 days.

According to the foregoing production method, the yeast strains for ethanol fermentation used herein may be *Saccharomyces sache* KFCC 11513.

According to the foregoing production method, the yeast strains for ethanol fermentation used herein may be prepared, in culture medium form, with incubation and shaking, using *Saccharomyces cerevisiae* in a liquid medium including 5 g of peptone, 5 g of yeast extract, and 5 g of glucose, in 1000 ml of distilled water.

According to the foregoing production method, a relative ratio, by weight, of the prepared linoleic acid-free seeds to the yeast strain for ethanol fermentation may range from 1:8 to 12.

According to the foregoing production method, a relative ratio, by weight, of the sterilized watermelon seeds to glacial acetic acid may range from 1:1 to 3.

According to the foregoing production method, after inoculation and during agitation of the linoleic acid-free watermelon seeds with the yeast strain for ethanol fermentation, a mineral solution including 1.0 g of $(NH_4)_2SO_4$, 1.0 g of $K_2HPO_4$, 1.0 g of $K_2HPO_4$, 0.2 g of $MgSO_4 \cdot H_2O$, 0.1 g of yeast extract, 10.0 mg of $FeSO_4$, 2.0 mg of $CaCl_2$, 2.0 mg of $MgSO_4$, and 2.0 mg of $ZnSO_4$, in 1 liter of distilled water, may be added to the inoculated watermelon seeds.

DETAILED DESCRIPTION

The present invention provides a method for the production of bioethanol using watermelon seeds, which includes: sterilizing the watermelon seeds, which are usually discarded as food waste from domestic houses, supermarkets, farm houses, and the like, at 121° C. for 10 to 20 minutes under anaerobic conditions; finely grinding the sterilized watermelon seeds; adding glacial acetic acid to the ground watermelon seeds to remove linoleic acid therefrom; and inoculating the linoleic acid-free watermelon seeds with a yeast strain for ethanol fermentation, such as *Saccharomyces cerevisiae*, followed by agitation at 100 to 300 rpm at 25 to 35° C. for 5 to 15 days to conduct fermentation, so as to enable the production of bioethanol with high production yields and considerable reduction in the release of hazardous substances such as carbon dioxide, formaldehyde, and the like, thereby accomplishing an eco-friendly and economically advantageous production of bioethanol without wasting food resources, such as corn, sugar cane, or the like.

Hereinafter, embodiments of the present invention will be described in detail.

The present invention may produce bioethanol using watermelon seeds that are commonly discarded as food waste. Although there are differences in the origins of watermelon, watermelon seeds generally contain 41.6% of carbohydrates, such as sucrose, glucose, fructose, and the like, 27.4% of fatty acids, 18.9% of proteins, and the remaining balance being other fractions such as minerals, vitamins, or the like. Among these, the carbohydrate fraction is converted into ethanol through anaerobic respiration of yeast having ethanol fermentation capabilities.

First, the watermelon seeds are subjected to sterilization at 121° C. for 10 to 20 minutes under anaerobic conditions. If the seeds are not suitably sterilized under such anaerobic conditions, fungi may be generated in large quantities, thereby reducing the ethanol production yield following the inoculation of the watermelon seeds with the yeast for ethanol fermentation.

Second, the sterilized watermelon seeds are finely ground using a grinder or the like. If the watermelon seeds are not finely ground, the carbohydrates contained within the watermelon seeds may not efficiently react with the yeast, or the lower surface area of the watermelon seeds may hamper the removal of linoleic acid using glacial acetic acid, resulting in poor fermentation.

Grinding procedures and/or conditions may be suitably adopted from conventional techniques, without limitation.

Third, the linoleic acid is removed from the ground watermelon seeds. For example, the ground watermelon seeds may be treated with glacial acetic acid and subjected to extraction of the linoleic acid. Since linoleic acid molecules are relatively stable, due to a relatively large number of carbon atoms therein, the yeast may not effectively use them as a carbon source thereby inhibiting the production of bioethanol. Although linoleic acid may be removed through alcohol extraction, glacial acetic acid extraction is preferable in removing linoleic acid. More preferably, 1 to 3-fold glacial acetic acid is added to a total weight of the ground watermelon seeds.

After removal of linoleic acid, the treated watermelon seeds may be inoculated with a yeast strain for ethanol fermentation. The yeast strains may include yeast having ethanol fermentation capabilities, without being particularly limited thereto. In the case where watermelon seeds are used as biomass, the yeast may be any yeast having ethanol fermentation capabilities. In consideration of production yield, *Saccharomyces cerevisiae* may be used.

After inoculating the yeast strain for ethanol fermentation, the inoculated watermelon seeds are left for 5 to 15 days at 25 to 35° C. while being gently stirred at 100 to 300 rpm. If the fermentation temperature is outside the aforementioned range, the rate of proliferation of the yeast strains may be undesirably decreased. It is recommended that the yeast strains sufficiently intake carbohydrate for at least 5 days. A proliferation period exceeding 15 days may not be suitable for anaerobic respiration.

Although an amount of the yeast strain for ethanol fermentation used herein depends upon yeast strain differences, a mixing ratio, by weight, of the prepared linoleic acid-free watermelon seeds to the yeast strain for ethanol fermentation may range from 1:8 to 12. In particular, *Saccharomyces cerevisiae* KCCM 1129, *Saccharomyces cerevisiae* KFCC 11352, or *Saccharomyces sache* KFCC 11513, mixed with the watermelon seeds in the aforementioned mixing ratio, may enable optimum production of ethanol. On the other hand, if the mixing ratio is beyond the aforementioned range, the carbohydrate fraction in the watermelon seeds utilized by the strain will be insufficient, in turn decreasing production yield.

The inoculation of the yeast strain for ethanol fermentation is generally used in culture medium form, prepared by incubation with shaking of the yeast strain, in a liquid medium including 5 g of peptone, 5 g of yeast extract and 5 g of glucose in 1000 ml of distilled water. In addition, in order to improve the proliferation rate of the yeast strains, a mineral solution including 1.0 g of $(NH_4)_2SO_4$, 1.0 g of $KH_2PO_4$, 1.0 g of $K_2HPO_4$, 0.2 g of $MgSO_4 \cdot H_2O$, 0.1 g of yeast extract, 10.0 mg of $FeSO_4$, 2.0 mg of $CaCl_2$, 2.0 mg of $MgSO_4$, and 2.0 mg of $ZnSO_4$ in 1 liter of distilled water may be added to the inoculated watermelon seeds while stirring the watermelon seeds.

The resultant bioethanol product, obtained according to the aforementioned processes, may be collected by conventional separation methods (e.g., fractional distillation).

Hereinafter, preferred embodiments of the present invention will be explained to more concretely understand the present invention with reference to the following examples. However, it will be apparent to those skilled in the art that such embodiments are provided for illustrative purposes only, and various modifications and alterations may be possible without departing from the scope and spirit of the present invention, and such modifications and alterations are duly included in the present invention as defined by the appended claims.

EXAMPLES

Example 1

Confirming the Possibility of Bioethanol Production from Watermelon Seeds

*Saccharomyces sache* KFCC 11513 and *Saccharomyces cerevisiae* KCCM 1129 were left at room temperature ranging from 25 to 30° C., thus being activated. After sterilizing watermelon seeds at 121° C. for 10 to 20 minutes under anaerobic conditions and grinding the same using a grinder, the ground watermelon seeds were divided into two groups, each of which weighed 20 g, using an electronic scale.

Both groups including the watermelon seeds were placed in Petri dishes, and one of the groups was inoculated with 100 g of a culture medium containing *Saccharomyces sache* KFCC 11513, while the other was inoculated with 100 g of another culture medium containing *Saccharomyces cerevisiae* KCCM 1129. Thereafter, plenty of water was added to each of the test groups, followed by sealing and leaving the same at room temperature.

After leaving the test groups about 7 days, the ethanol generated in each dish was collected through fractional distillation and weighed. According to the aforementioned procedures, 10.2 ml of ethanol was collected from the dish inoculated with *Saccharomyces sache* KFCC 11513, while 11.4 ml of ethanol was collected from the dish inoculated with *Saccharomyces cerevisiae* KCCM 1129. Consequently, it was confirmed that bioethanol may be produced using watermelon seeds.

Example 2

Bioethanol Production after Removal of Linoleic Acid from Watermelon Seeds

As shown in Example 1, bioethanol may be produced using watermelon seeds and the present example was performed to find how to maximize the production yield of bioethanol. Among the ingredients of the watermelon seeds, linoleic acid was examined to determine whether it influences the bioethanol production yield.

First, *Saccharomyces cerevisiae* KCCM 1129 were left at room temperature ranging from 25 to 30° C., thus being activated. The watermelon seeds were sterilized and ground according to the same procedures as described in Example 1. Next, a filter paper was spread in a funnel and the funnel was fixed above a beaker using a clamp and a stand. After placing 20 g of the ground watermelon seeds on the filter paper, 60 ml of glacial acetic acid was poured over the seeds using a glass rod.

After preparing two Petri dishes, linoleic acid-free watermelon seeds were placed in one of the dishes, while the same amount of watermelon seeds without removal of linoleic acid were placed in the other dish, followed by comparing the ethanol production yields therebetween using the same procedures as described in Example 1. The comparison results exhibited that 12.3 ml of ethanol was formed in the dish containing the linoleic acid-free watermelon seeds, while 11.0 ml of ethanol was obtained from the dish containing watermelon seeds without removal of linoleic acid.

Consequently, it can be seen from the present example that the ethanol production yield may be increased by removing linoleic acid from watermelon seeds, before fermentation thereof, with the yeast having ethanol fermentation capabilities.

Example 3

Difference in Ethanol Production Yield Depending Upon Strain Differences

The respective strains, *Saccharomyces cerevisiae* KCCM 1129, *Saccharomyces cerevisiae* KFCC 11352, and *Saccharomyces sache* KFCC 11513, were left at room temperature ranging from 25 to 30° C., thus being activated. After sterilizing watermelon seeds at 121° C. for 10 to 20 minutes under anaerobic conditions and grinding the same using a grinder, the ground watermelon seeds were subjected to extraction with glacial acetic acid to remove linoleic acid therefrom.

Next, the linoleic acid-free watermelon seeds were divided into three groups, each of which weighed 10 g, using an electronic scale.

The respective groups including the linoleic acid-free watermelon seeds were placed in three Petri dishes and were inoculated with 100 g of a culture medium containing *Saccharomyces cerevisiae* KCCM 1129, 100 g of a culture medium containing *Saccharomyces cerevisiae* KFCC 11352, and 100 g of a culture medium containing *Saccharomyces sache* KFCC 11513, respectively. Thereafter, 900 g of distilled water was added to each of the test groups, followed by fermentation at 180 rpm at 30° C. for 10 days.

As a result, it was found that 42.5 ml of ethanol was separated from the dish (via fractional distillation) inoculated with *Saccharomyces cerevisiae* KCCM 1129, 36.5 ml of ethanol was separated from the dish (via fractional distillation) inoculated with *Saccharomyces cerevisiae* KFCC 11352, and 38.2 ml of ethanol was separated from the dish (via fractional distillation) inoculated with *Saccharomyces sache* KFCC 11513, respectively.

Consequently, it can be seen that the yeast strain, *Saccharomyces cerevisiae* KCCM 1129, may be most suitable to produce ethanol from linoleic acid-free watermelon seeds as a raw material.

Moreover, a final amount of ethanol obtained using *Saccharomyces cerevisiae* KCCM 1129 is 4.25 ml/g. Assuming that watermelon production is approximately 37.2217 t/ha, and each watermelon has an average weight of about 8 kg, and contains seeds of about 20 g, watermelon seeds may be obtained in an amount of approximately 930, 542.5 g/ha, thus resulting in bioethanol production of about 4,187.5 L/ha from the watermelon seeds. Consequently, it can be seen that watermelon seeds are more effective than corn, which generally produces about 3,100 to 4,000 L/ha of bioethanol, in terms of bioethanol production.

Example 4

Difference in Ethanol Production Yield Depending Upon Ratio by Weight of Strain to Watermelon Seeds

*Saccharomyces cerevisiae* KCCM 1129 were left at room temperature ranging from 25 to 30° C., thus being activated. After sterilizing watermelon seeds at 121° C. for 10 to 20 minutes under anaerobic conditions, and grinding the same using a grinder, the ground watermelon seeds were divided into three groups which weighed 5 g, 10 g and 20 g, respectively, using an electronic scale.

Respective groups including the watermelon seeds were placed in three Petri dishes and were inoculated with 100 g of a culture medium containing *Saccharomyces cerevisiae* KCCM 1129. Thereafter, 900 g of distilled water was added to each of the test groups, followed by fermentation at 180 rpm at 30° C. for 10 days.

As a result, it was found that 9.7 ml, 22.6 ml, and 11.4 ml of ethanol were collected from these dishes (via fractional distillation) containing 5 g, 10 g, and 20 g of watermelon seeds, respectively.

These results exhibited that, when a ratio by weight of watermelon seeds to *Saccharomyces cerevisiae* KCCM 1129 is 1:10 during fermentation therebetween, bioethanol production using watermelon seeds is most preferably accomplished. For the dish containing 5 g of watermelon seeds, the amount of carbohydrate exposed to the yeast strain was not sufficient to conduct fermentation. Conversely, in the dish containing 20 g of watermelon seeds, chemically stable linoleic acid was considered to adversely affect the activity of the yeast strain for ethanol production.

According to the present invention, it is possible to obtain eco-friendly biomass with high bioethanol production yield substantially equal to or more than that accomplished using corn, poplar wood, or the like. According to the present invention, carbon dioxide emissions may be optimally reduced by 90% or more, compared to ethanol production through industrial processes. Moreover, the release of toxic substances such as benzene, carbon monoxide, and the like, during combustion may be remarkably decreased.

The present invention may provide an eco-friendly method for production of bioethanol by utilizing watermelon seeds which are commonly discarded as food waste, enabling the production of ethanol fuels useful for mankind, while considerably reducing food waste (i.e., watermelon seeds or the like).

Therefore, the present invention does not cause ethical problems, such as wasting food resources, which is contrary to the utilization of existing crop biomass or wood-based biomass.

In addition, the present invention is based on findings regarding the most effective fermentation yeast strains and conditions for the production of bioethanol using watermelon seeds, thus enabling highly efficient production of bioethanol.

While the present invention has been described with reference to the preferred embodiments, it will be understood by those skilled in the related art that various modifications and variations may be made therein without departing from the scope of the present invention as defined by the appended claims.

What is claimed is:

1. A method for producing bioethanol, comprising:
   sterilizing watermelon seeds at 121° C. for 10 to 20 minutes under anaerobic conditions, grinding the sterilized watermelon seeds,
   adding glacial acetic acid to the ground seeds to remove linoleic acid therefrom; and
   inoculating the prepared seeds free from linoleic acid with a strain for ethanol fermentation, wherein the strain is yeast having an ethanol fermentation capability.

2. The method according to claim 1, wherein, after inoculating the prepared seeds free from linoleic acid with the strain for ethanol fermentation, the inoculated seeds are subjected to fermentation while agitating at 25 to 35° C. and 100 to 300 rpm for 5 to 15 days.

3. The method according to claim 1, wherein the strain for ethanol fermentation is *Saccharomyces cerevisiae* or *Saccharomyces sache*.

4. The method according to claim 1, wherein the strain for ethanol fermentation is prepared in a culture medium form by shaking incubation of *Saccharomyces cerevisiae* in a liquid medium comprising 5 g of peptone, 5 g of Yeast extract and 5 g of glucose in 1000 ml of distilled water.

5. The method according to claim 2, wherein a ratio by weight of the prepared seeds free from linoleic acid to the strain for ethanol fermentation ranges from 1:8 to 12.

6. The method according to claim 1, wherein a ratio by weight of the sterilized watermelon seeds to glacial acetic acid ranges from 1:1 to 3.

7. The method according to claim 2, wherein during agitating after inoculating the prepared seeds free from linoleic acid with the strain for ethanol fermentation, a mineral solution comprising 1.0 g of $(NH_4)_2SO_4$, 1.0 g of $KH_2PO_4$, 1.0 g of $K_2HPO_4$, 0.2 g of $MgSO_4 \cdot H_2O$, 0.1 g of yeast extract, 10.0 mg of $FeSO_4$, 2.0 mg of $CaCl_2$, 2.0 mg of $MgSO_4$ and 2.0 mg of $ZnSO_4$ in 1 liter of water is added to the inoculated watermelon seeds.

8. The method according to claim 1, wherein the strain for ethanol fermentation is *Saccharomyces cerevisiae*.

* * * * *